(12) United States Patent
Kasahara

(10) Patent No.: US 9,349,190 B2
(45) Date of Patent: May 24, 2016

(54) ULTRASOUND IMAGE PROCESSING APPARATUS

(75) Inventor: Eiji Kasahara, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 44 days.

(21) Appl. No.: 14/125,131

(22) PCT Filed: Jul. 13, 2012

(86) PCT No.: PCT/JP2012/067897
§ 371 (c)(1),
(2), (4) Date: Dec. 10, 2013

(87) PCT Pub. No.: WO2013/015135
PCT Pub. Date: Jan. 31, 2013

(65) Prior Publication Data
US 2014/0105478 A1    Apr. 17, 2014

(30) Foreign Application Priority Data

Jul. 27, 2011    (JP) ................................ 2011-163990

(51) Int. Cl.
*G06K 9/00*    (2006.01)
*G06T 7/20*    (2006.01)
*A61B 8/08*    (2006.01)
(Continued)

(52) U.S. Cl.
CPC ................ *G06T 7/20* (2013.01); *A61B 8/0883* (2013.01); *A61B 8/145* (2013.01); *A61B 8/4444* (2013.01); *A61B 8/4483* (2013.01); *A61B 8/486* (2013.01); *G06T 7/0012* (2013.01); *A61B 8/463* (2013.01); *A61B 8/5223* (2013.01)

(58) Field of Classification Search
USPC .......................................... 382/128–134, 103
See application file for complete search history.

(56) References Cited

U.S. PATENT DOCUMENTS 6,980,679 B2 * 12/2005 Jeung et al. .................... 382/128
7,251,352 B2 *  7/2007 Sauer et al. .................... 382/128
(Continued)

FOREIGN PATENT DOCUMENTS

CN        101060813 A    10/2007
JP        2003-190167 A   7/2003
(Continued)

OTHER PUBLICATIONS

International Search Report dated Sep. 4, 2012 issued in corresponding application No. PCT/JP2012/067897.
(Continued)

*Primary Examiner* — Alex Liew
(74) *Attorney, Agent, or Firm* — Westerman, Hattori, Daniels & Adrian, LLP

(57) ABSTRACT

Ultrasonic image data from a plurality of time phases are stored in an image storage unit (22). A pattern matching unit (30) searches the image data in a search time phase for moving points corresponding to set points in the image data in a reference time phase, on the basis of a correlation operation performed on the image data. In this way, moving points for set points are searched across a plurality of time phases. A diagnostic information generating unit (40) then determines the main direction of movement of the set points across the plurality of time phases based on the moving points searched across the plurality of time phases, and diagnostic information is obtained by evaluating the movement of the set points with reference to the main direction.

13 Claims, 8 Drawing Sheets

(51) Int. Cl.
*A61B 8/14* (2006.01)
*A61B 8/00* (2006.01)
*G06T 7/00* (2006.01)

(56) References Cited

U.S. PATENT DOCUMENTS

| | | | |
|---|---|---|---|
| 7,301,530 B2* | 11/2007 | Lee et al. | 345/158 |
| 2003/0210812 A1* | 11/2003 | Khamene et al. | 382/128 |
| 2007/0071295 A1* | 3/2007 | Jackson | 382/128 |
| 2008/0188743 A1 | 8/2008 | Waki et al. | |
| 2008/0287803 A1* | 11/2008 | Li et al. | 600/466 |
| 2009/0124903 A1 | 5/2009 | Osaka | |
| 2009/0270732 A1* | 10/2009 | Abe et al. | 600/443 |
| 2009/0303252 A1* | 12/2009 | Hyun et al. | 345/643 |
| 2011/0257525 A1* | 10/2011 | Kanade et al. | 600/443 |
| 2013/0346050 A1* | 12/2013 | Kim et al. | 703/11 |
| 2014/0105478 A1* | 4/2014 | Kasahara | 382/131 |

FOREIGN PATENT DOCUMENTS

| | | |
|---|---|---|
| JP | 2007-143606 A | 6/2007 |
| JP | 2009-444 A | 1/2009 |
| JP | 2009-129388 A | 6/2009 |
| JP | 2009-183566 A | 8/2009 |
| JP | 2007-130063 A | 5/2013 |
| WO | 2009/098973 A1 | 8/2009 |

OTHER PUBLICATIONS

Japanese Notice of Grounds for Rejection dated Aug. 6, 2013 issued in Japanese application No. 2011-163990, with English Translation.
Japanese Notice of Grounds for Rejection dated Aug. 28, 2012 issued in Japanese application No. 2011-163990, with English Translation.
Notification of Transmittal of Translation of the International Preliminary Report on Patentability (form PCT/IB/338)of PCT/JP2012/06789, dated Jul. 13, 2012, with forms PCT/IB/326, PCT/IB/373, PCT/ISA/237 (w/English translation) and PCT/IB/308, (13 pages).
Chinese Office Action dated Dec. 22, 2014, issued in corresponding CN Patent Application No. 201280037593.8 with English translation (12 pages).
Office Action dated Sep. 8, 2015, issued in counterpart Chinese Patent Application No. 201280037593.8 w/English translation (9 pages).

* cited by examiner

ULTRASOUND IMAGE PROCESSING APPARATUS

TECHNICAL FIELD

The present invention relates to an ultrasound image processing apparatus, and in particular, to a device which executes a correlation calculation between image data.

BACKGROUND ART

An ultrasound image processing apparatus and an ultrasound diagnostic apparatus are known which execute a correlation calculation on image data of ultrasound images obtained by transmitting and receiving ultrasound. For example, Patent Documents 1 and 2 disclose epoch-making techniques in which a motion of a cardiac muscle is traced over a plurality of frames by pattern matching based on the correlation calculation. In addition, techniques for forming a panorama image by partially overlapping, by pattern matching, a plurality of sets of image data obtained while a probe is moved.

In the pattern matching between image data, for example, a template is set at a location of interest in one of the sets of image data, and a correlation of the image data in the template is calculated while the template is moved in the other set of image data. A position of the template in the other set of image data having the largest similarly is set as a position corresponding to the location of interest.

With this process, for example, a position corresponding to the location of interest is searched (tracked) over a plurality of time phases, to enable observation of the movement of the location of interest. For example, a fixed point which forms a reference point is set, and a distance from the fixed point is calculated, to enable quantitative evaluation of the movement of the location of interest.

RELATED ART REFERENCES

Patent Document

[Patent Document 1] JP 2007-130063 A
[Patent Document 2] JP 2007-143606 A

DISCLOSURE OF INVENTION

Technical Problem

In view of the related art described above, the present inventors have researched and developed the correlation calculation between ultrasound image data. In particular, the present inventors have focused attention in the function to observe the movement of the location of interest.

The present invention was made in the course of the research and development, and an advantage of the present invention is provision of a technique for appropriately evaluating movement of a set point which is set on a location of interest.

Solution to Problem

According to one aspect of the present invention, there is provided an ultrasound image processing apparatus comprising an image storage unit which stores ultrasound image data of a plurality of time phases, an image processor which searches image data of a search time phase for a movement point corresponding to a set point which is set in image data of a reference time phase, based on a correlation calculation between image data, and a diagnostic information generator which determines a primary direction of movement of the set point over a plurality of time phases based on the movement points searched over a plurality of time phases and obtains diagnostic information by evaluating the movement of the set point with the primary direction as a reference.

According to above-described configuration, because the movement of the set point is evaluated with the primary direction of movement over a plurality of phases as a reference, for example, there can be obtained diagnostic information in which influence of the movement is relatively strongly reflected and the movement is sensitively captured.

According to another aspect of the present invention, preferably, the diagnostic information generator determines the primary direction according to a spatial variation of the movement points searched over a plurality of time phases.

According to another aspect of the present invention, preferably, the diagnostic information generator sets a fixed point which becomes a reference for diagnosis on a line corresponding to the primary direction.

According to another aspect of the present invention, preferably, the diagnostic information generator forms a displacement waveform showing a change with respect to time of a distance from the fixed point to the movement point.

According to another aspect of the present invention, preferably, the image processor comprises a template generation function to generate, based on a set point which is set in the image data of the reference time phase, a template corresponding to the set point, a search area setting function to set a search area in the image data of a search time phase, a correlation calculation function to execute a correlation calculation for each position in the search area while moving the template in the search area, based on image data of a template of the reference time phase and image data overlapping a template of the search time phase, and a weighting process function to apply a weighting process on a result of the correlation calculation obtained at each position in the search area based on the distance from a reference position to the position, wherein a movement point corresponding to the set point is searched in the search area based on a result of the correlation calculation to which the weighting process is applied.

According to another aspect of the present invention, there is provided a program which, when executed, causes a computer which processes ultrasound image data of a plurality of time phases to realize an image processing function to search image data of a search time phase for a movement point corresponding to a set point which is set in image data of a reference time phase, based on a correlation calculation between image data, and a diagnostic information generating function to determine a primary direction of movement of the set point over a plurality of time phases based on the movement points searched over a plurality of time phases and to obtain diagnostic information by evaluating the movement of the set point with the primary direction as a reference.

The above-described program is stored on a computer-readable storage medium such as, for example, a disk and a memory, and is provided to a computer through the storage medium. Alternatively, the program may be provided to the computer through an electrical communication line such as the Internet.

Advantageous Effects of Invention

According to various aspects of the present invention, movement of a set point which is set at a location of interest can be appropriately evaluated. For example, according to a preferred configuration of the present invention, because movement of the set point is evaluated with the primary direction of movement over a plurality of time phases as a reference, there can be obtained diagnostic information in which influence of movement is relatively strongly reflected and the movement is sensitively captured.

BEST MODE FOR CARRYING OUT THE INVENTION

Figure 1:
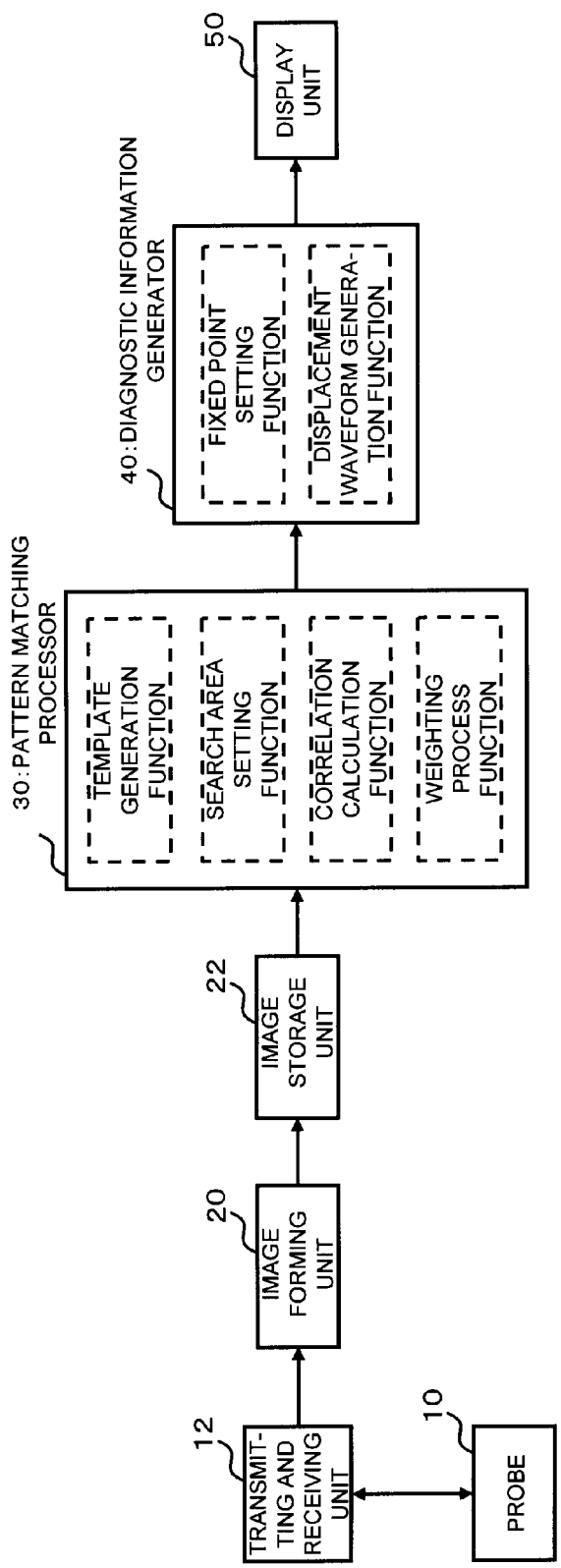
FIG. 1 is diagram showing an overall structure of an ultrasound diagnostic apparatus according to a preferred embodiment of the present invention.

FIG. 1 is diagram showing an overall structure of an ultrasound diagnostic apparatus preferable in practicing the present invention. The ultrasound diagnostic apparatus of FIG. 1 has functions of an ultrasound image processing apparatus according to a preferred embodiment of the present invention.

A probe 10 is an ultrasound probe which transmits and receives ultrasound to and from an area including a target object such as, for example, a heart and a muscle. The probe 10 comprises a plurality of transducer elements which transmit and receive ultrasound, and transmission of the plurality of transducer elements is controlled by a transmitting and receiving unit 12, to form a transmission beam. The plurality of transducer elements also receive the ultrasound obtained from the area including the target object, a signal thus obtained is output to the transmitting and receiving unit 12, and the transmitting and receiving unit 12 forms a reception beam, to collect echo data along the reception beam.

The probe 10 scans the ultrasound beam (transmission beam and reception beam) in a two-dimensional plane, and collects the echo data. Alternatively, there may be used a three-dimensional probe which three-dimensionally scans the ultrasound beam in a three-dimensional space.

When the ultrasound beam is scanned in the area including the target object and the echo data are collected by the transmitting and receiving unit 12, an image forming unit 20 forms ultrasound image data based on the collected echo data. The image forming unit 20 forms image data of, for example, a B mode image. The image forming unit 20 also forms a plurality of sets of image data corresponding to a plurality of ultrasound images. For example, the image forming unit 20 forms a plurality of sets of image data showing the target object over a plurality of points of time (plurality of time phases). Alternatively, a plurality of sets of image data showing the target object at different positions may be formed while the probe 10 is gradually moved. The plurality of sets of image data formed by the image forming unit 20 are stored in an image storage unit 22.

A pattern matching processor 30 functions as an image processor which executes the pattern matching between image data. The pattern matching processor 30 has a function to generate a template which is set in image data, a function to set a search area in the image data, a function to execute a correlation calculation based on the image data in the template, and a function to apply a weighting process on a result of the correlation calculation. The pattern matching processor 30 executes the pattern matching between image data based on the correlation calculation on the plurality of sets of image data stored in the image storage unit 22.

Figure 2:
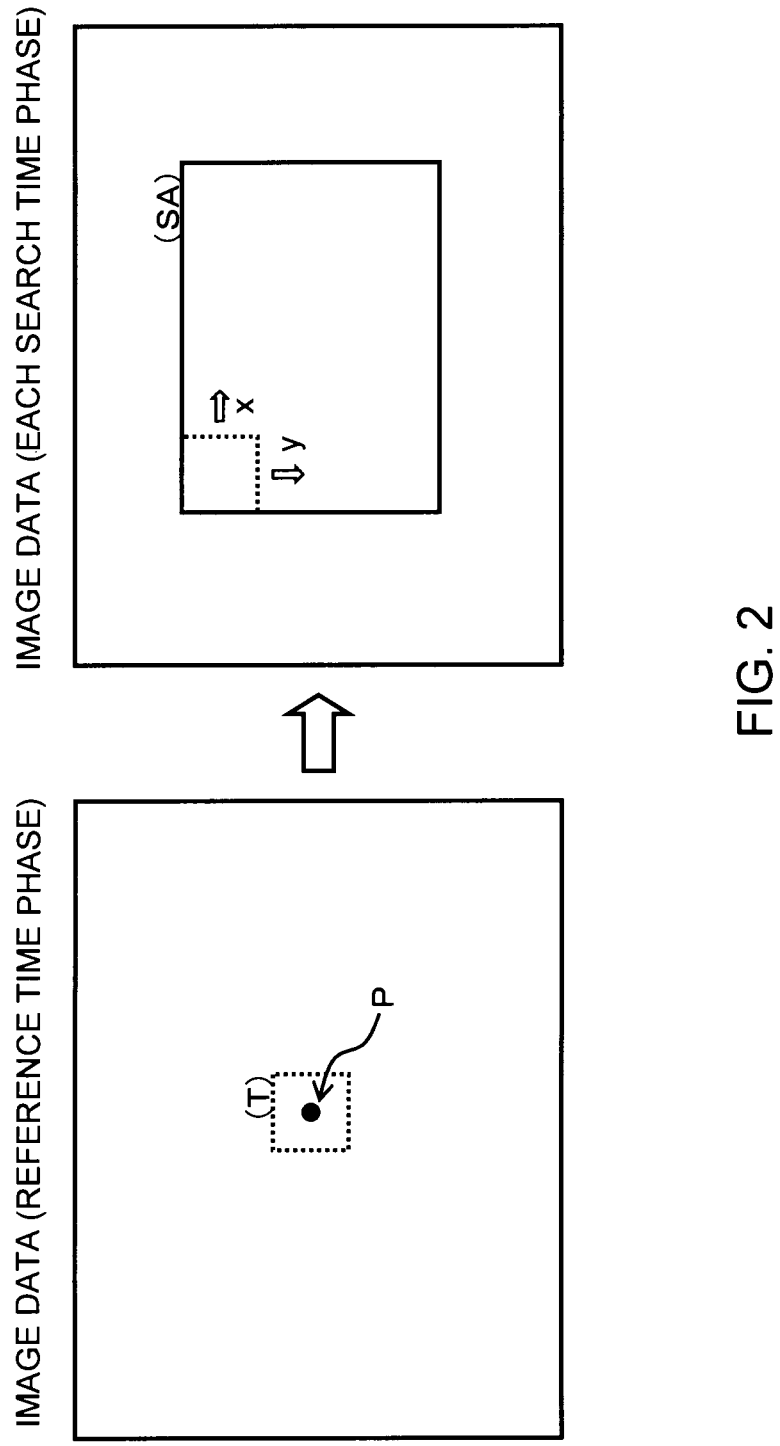
FIG. 2 is a diagram for explaining a pattern matching between image data.

FIG. 2 is a diagram for explaining the pattern matching between image data, and shows a process between image data of a reference time phase and image data of each search time phase. The image data of the reference time phase and the image data of the search time phase are, for example, image data obtained from the same heart at different points of time. In the pattern matching, first, a set point P is set by a user such as an inspector in the image data of the reference time phase, and a template T is set surrounding the set point in the image data of the reference time phase. FIG. 2 shows a template T having a square shape centered at the set point. A size of the template T in terms of a number of pixels is, for example, about 20 pixels in the vertical direction and 20 pixels in the horizontal direction. The size, shape, and position of the template T are not limited to those of the specific example configuration of FIG. 2. Alternatively, the size, shape, and position of the template T may be changed by the user.

When the template T is set, a search area SA is set in the image data of each search time phase. The search area SA is fixedly set, for example, at the same position in the image data over a plurality of search time phases. In this case, for example, the size and shape of the search area SA are also fixedly set. In order to fix the position of the search area SA, the size (breadth) of the search area SA is preferably relatively large. Alternatively, the entire image data of each search time phase may be set as the search area SA.

The search area SA may be set, over a plurality of search time phases and for each search time phase, to surround a position of a movement point searched in the image data of the time phase adjacent to the search time phase. In other words, as will be described later, because a movement point corresponding to a set point P which is set in the image data of the reference time phase is searched in the search area SA which is set for the image data of each search time phase, when the movement points are sequentially searched over a plurality of search time phases, the search area SA may be determined for a certain search time phase using, as a reference, a movement point which is searched one time phase prior to that search time phase.

Figure 3:
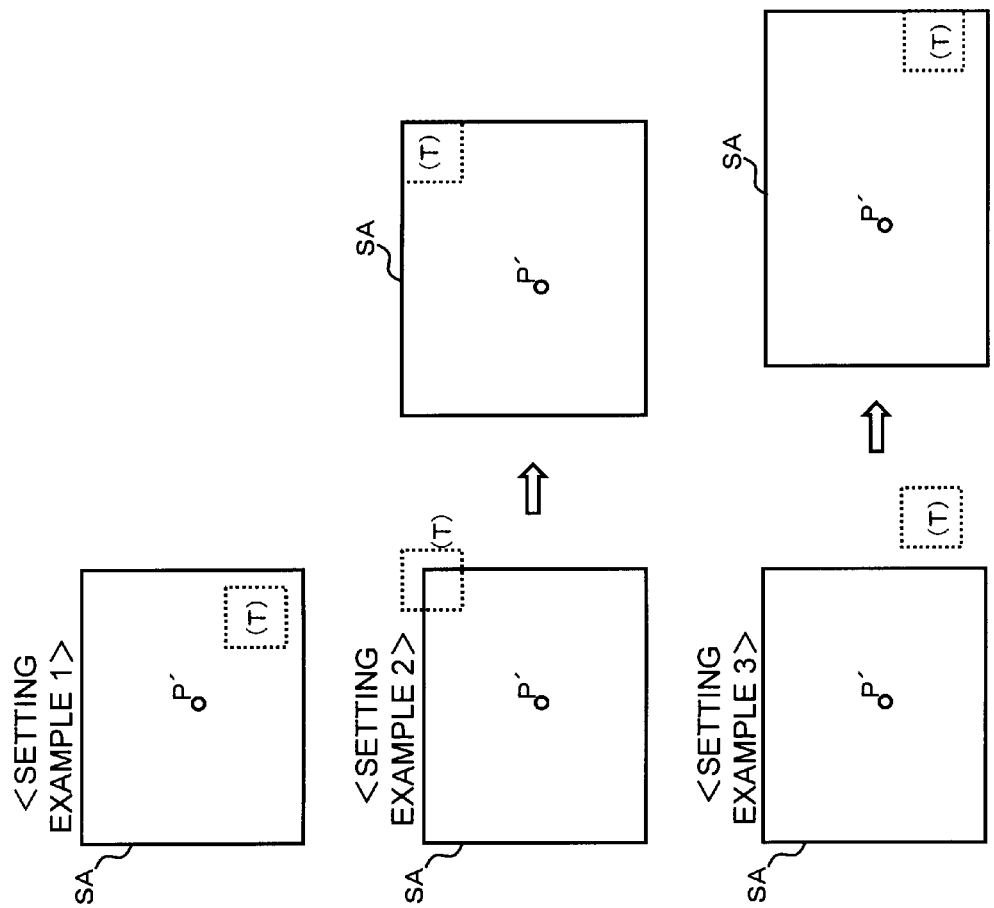
FIG. 3 is a diagram showing an example setting of a search area according to a position of a movement point.

FIG. 3 is a diagram showing an example setting of the search area SA corresponding to a position of the movement point. Specifically, a specific example configuration is shown in which, for each search time phase, the search area SA of the search time phase is set corresponding to a movement point P' searched in the previous time phase of the search time phase. In FIG. 3, a rectangle shown by a dotted line shows an area corresponding to the template T which is set in the image data of the reference time phase.

In a setting example 1, a rectangular search area SA centered at the movement point P' searched in the previous time phase is set, and the area corresponding to the template T is located within the search area SA.

In a setting example 2 also, a rectangular search area SA centered at the movement point P' searched in the previous time phase is set. However, in this state, the area corresponding to the template T extends beyond the search area SA. When the template T extends beyond the search area SA in this manner, the search area SA is expanded such that the area corresponding to the template T is within the search area SA. For example, in the setting example 2, an upper side and a right side are translated to expand the search area SA and such that the template T is included.

In a setting example 3 also, first, a rectangular search area SA centered at the movement point P' searched in the previous time phase is set. However, in this state, the area corresponding to the template T is outside of the search area SA. When the template T is completely outside of the search area SA as in this example setting also, the search area SA is expanded such that the area corresponding to the template T is within the search area SA. For example, in the setting example 3, the right side is translated to expand the search area SA and such that the template T is included.

Because it is highly likely that the movement point which is searched is located near the movement point which is searched in the previous time phase, the search area SA is set centered at the movement point which is searched in the previous time phase as in the setting examples shown in FIG. 3, so that the movement point to be originally detected can be searched even when the search area SA is set relatively narrow. In addition, because the search area SA is expanded to include the area corresponding to the template T of the reference time phase, even in a case, for example, in which an organ which involves periodical motion such as a heart is diagnosed over a plurality of time phases and the organ returns to the state corresponding to the reference time phase, an area corresponding to the template T of the reference time phase can be included as a candidate of the movement point.

Referring again to FIG. 2, when the template T and the search area SA are set, the template T is moved in the search area SA of the image data of each search time phase, and, at each position, a correlation value is calculated based on a plurality of pixels within the template T of the image data of the reference time phase and a plurality of pixels in an area overlapping the template T of the image data of each search time phase. For example, a position shown by a dotted rectangle in the search area SA in FIG. 2 is set as an initial position, the template T is moved stepwise from the initial position in the x direction and the y direction, a correlation value is calculated at each position, and a plurality of correlation values are calculated corresponding to a plurality of positions over the entire area in the search area SA.

The correlation value is a numerical value indicating a degree of correlation relationship (degree of similarity) between image data, and, for calculation of the correlation value, known equations may be used corresponding to each method of correlation calculation. For example, as in a phase only correlation or a cross-correlation, a correlation value which shows a larger value as the degree of similarity becomes larger may be used, or, as in a minimum-sum absolute-difference, a correlation value which shows a smaller value as the degree of similarity becomes larger may be used. In the present embodiment, a self-correlation value which shows a smaller value as the degree of similarity becomes larger is used as a specific example of the correlation value. In addition, in the present embodiment, a weighting process to be described later is applied on the result of the correlation calculation (self-correlation value) obtained in each position in the search area SA.

When the self-correlation value after the weighting process is calculated at each of a plurality of positions over the entire area of the search area SA in this manner, a position having the largest degree of similarity is identified from the plurality of positions and is set as a movement point which is a point to which the set point has moved.

Figure 4:
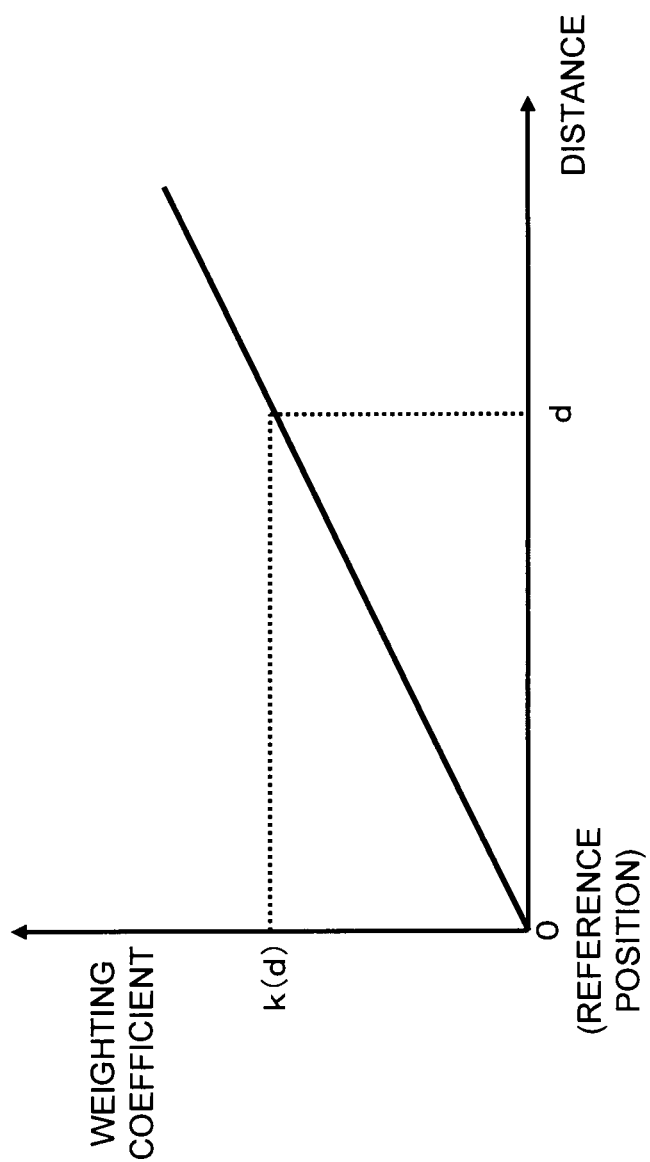
FIG. 4 is a diagram showing a specific example of a weighting coefficient used for a weighting process.

FIG. 4 is a diagram showing a specific example of a weighting coefficient used for the weighting process. A horizontal axis of FIG. 4 represents a distance from a reference position for each position for which the self-correlation value is calculated. The reference position is, for example, the position of the movement point searched in the previous time phase (for example, reference numeral P' in FIG. 3) or the position of the set point which is set in the image data of the reference time phase (for example, reference numeral P in FIG. 2). A vertical axis of FIG. 4 represents a weighting coefficient. As shown in FIG. 4, a weighting coefficient at a distance d is k(d).

In the present embodiment, as a specific example of the correlation value, a self-correlation value which shows a smaller value as the degree of similarity becomes larger is used. Thus, in the present embodiment, the weighting coefficient is set smaller for an area closer to the reference position having a higher possibility of having a high degree of similarity, and the weighting coefficient is increased as the position becomes farther away from the reference position. The self-correlation value at each position is multiplied by the weighting coefficient corresponding to the position, and the movement point which is a point to which the set point has moved is searched based on the multiplication result; that is, the self-correlation value to which the weighting process is applied.

With this process, for example, a search in which more importance is placed on an area near the reference position expected to have a relatively high degree of correlation can be enabled while reducing overlooking of search by setting a relatively wide search area. Thus, significant deviation of the searched movement point from the actual moved point of the set point can be inhibited, and, as a result, the precision of the search based on the correlation calculation can be improved.

The specific example of the weighting coefficient shown in FIG. 4 is merely exemplary, and, alternatively, for example, there may be used a weighting coefficient which non-linearly changes with distance or a weighting coefficient which step-wise changes (in steps) with distance. When a correlation value which shows a larger value as the degree of similarity becomes larger is used, a weighting coefficient which becomes larger as the position becomes closer to the reference position and which becomes smaller as the position becomes farther away from the reference position is preferable.

Figure 5:
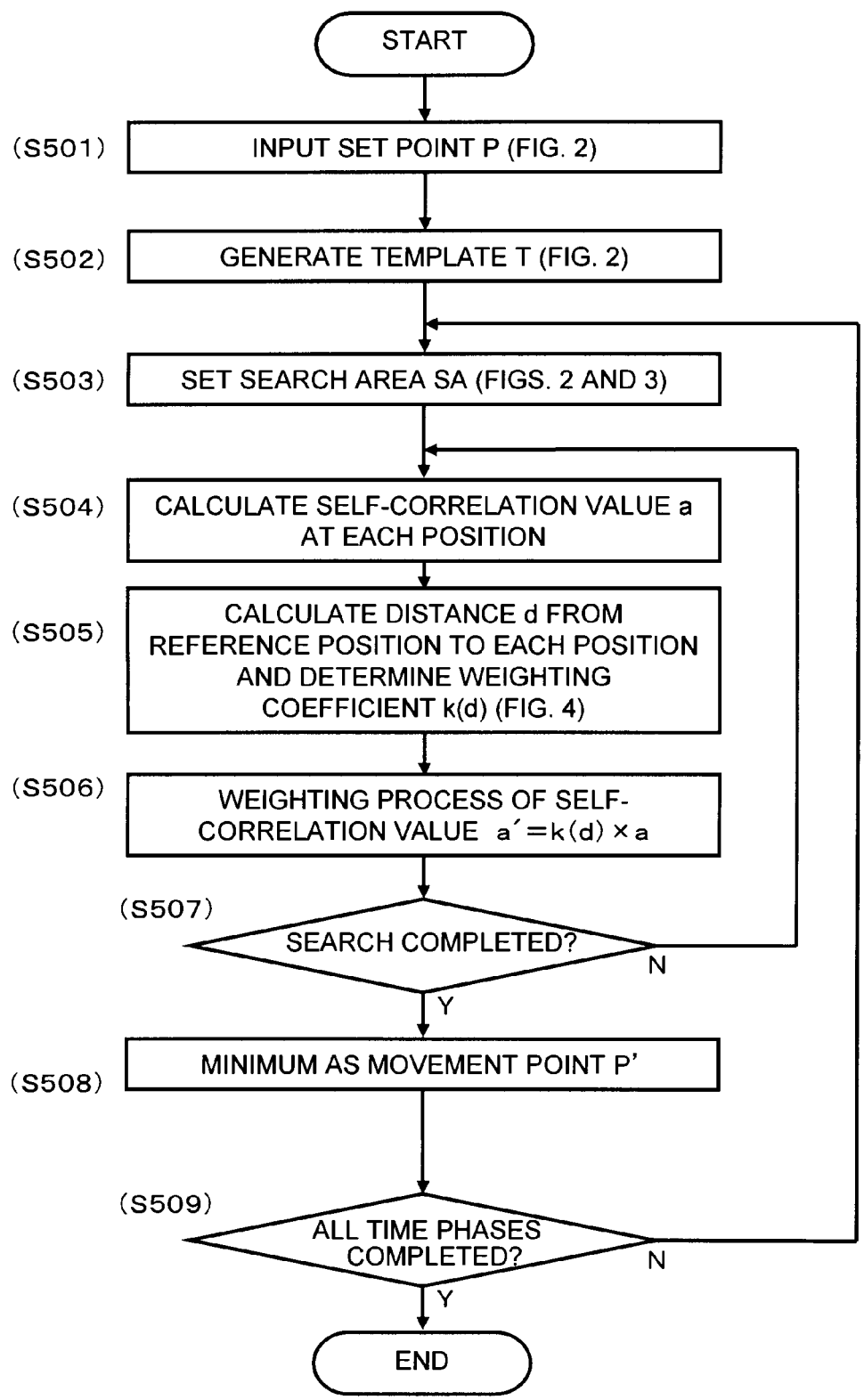
FIG. 5 is a flowchart showing a process at a pattern matching processor.

FIG. 5 is a flowchart showing a process by the pattern matching processor 30 (FIG. 1). When the user sets a set point P in the image data of the reference time phase (S501; refer to FIG. 2), a template T corresponding to the set point P is set in the image data of the reference time phase (S502; refer to FIG. 2).

Next, a search area SA is set in the image data of each search time phase (S503; refer to FIGS. 2 and 3), a template T is set in the search area SA, and a self-correlation value a is calculated in the position of the template T based on a plurality of pixels in the template T of the image data of the reference time phase and a plurality of pixels in an area overlapping the template T in the image data of each search time phase (S504).

Then, a distance d from the reference position to each position is calculated, a weighting coefficient k(d) for that position is determined (S505; refer to FIG. 4), the self-correlation value a is multiplied by the weighting coefficient k(d), and a self-correlation value a' after the weighting process is calculated (S506).

It is then checked whether or not the search over the entire area in the search area SA is completed (S507), and, if the search is not completed, the process returns to S504, the template T is moved to a next position, and the processes from S504 to S506 are executed at the new position.

When the processes from S504 to S506 are repeatedly executed and it is confirmed in S507 that the search over the entire area in the search area SA is completed, a position, among all positions in the search area SA, where the self-correlation value a' after the weighting process is the minimum is identified, and the identified position is set as the movement point of the set point (S508). In this manner, the movement point for the image data of each search time phase is identified.

It is then checked whether or not a search for all search time phases is completed (S509). If the search is not completed, the process returns to S503 and processes related to the image data of the next search time phase are executed. When the processes from S503 to S508 are repeatedly executed and it is confirmed in S509 that the search for all search time phases is completed, the process at the pattern matching processor 30 is completed.

Referring again to FIG. 1, when the search for image data of all search time phases is completed at the pattern matching processor 30, a diagnostic information generator 40 generates diagnostic information related to a target tissue based on the result of the search. The diagnostic information generator 40 has a function to set a fixed point which becomes a reference in the diagnosis, and a function to generate, as diagnostic information, a displacement waveform related to a movement point, with the fixed point as a reference. A display image including the displacement waveform formed in the diagnostic information generator 40 is displayed on a display unit 50.

Figure 6:
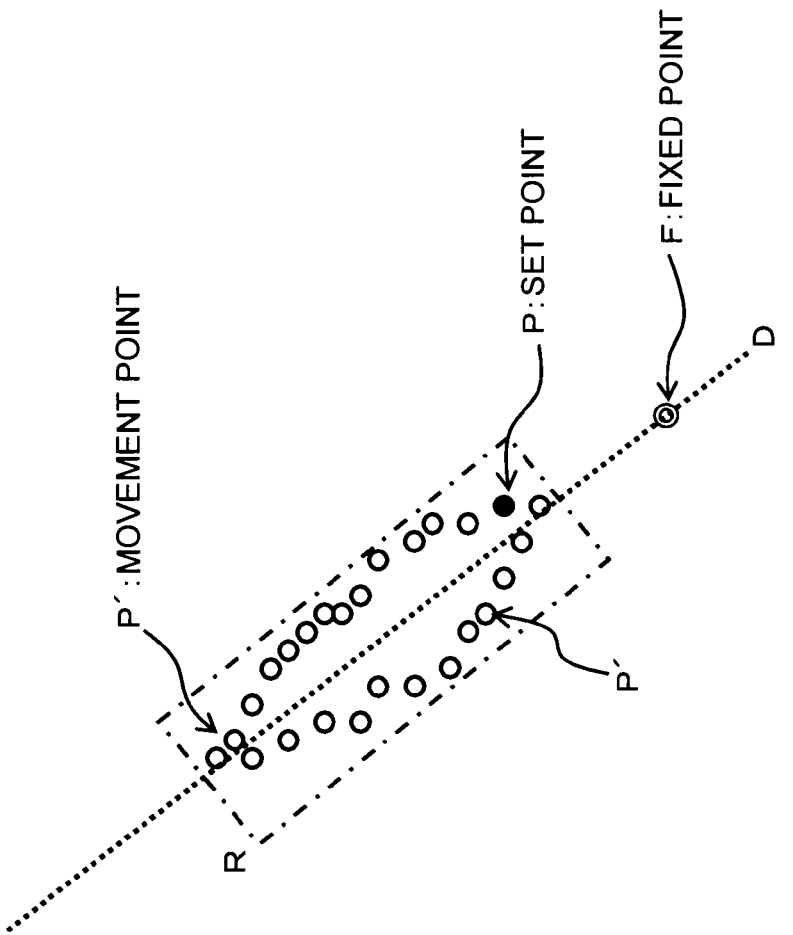
FIG. 6 is a diagram for explaining setting of a fixed point which is used as a reference in diagnosis.

FIG. 6 is a diagram for explaining setting of a fixed point which forms a reference in the diagnosis. FIG. 6 shows movement points P' of a plurality of time phases searched in the image data over a plurality of search time phases for a certain set point P.

The diagnostic information generator 40 (FIG. 1) determines a primary direction of movement of the set point P over the plurality of time phases based on the movement points P' of the plurality of time phases for the set point P. For example, as shown in FIG. 6, a rectangle R which surrounds all of the plurality of movement points P' and which circumscribes the movement points P' corresponding to the 4 sides is set, and a major axis passing through the center of the rectangle R is set as the primary direction D. The determination of the primary direction D is not limited to the method of using the rectangle R. For example, a known method commonly referred to as principle component analysis may be used, and a direction which most clearly represents the spatial variation of the movement points P'; that is, a direction where the variance of the movement points P' is the maximum, may be set as the primary direction D.

The diagnostic information generator 40 then sets a fixed point F on the determined primary direction D. Alternatively, the user may set a provisional fixed point F in advance, and the provisional fixed point F may be moved to the fixed point F determined by the diagnostic information generator 40. When the fixed point F is set, the diagnostic information generator 40 calculates a distance from the set fixed point F to each movement point P', and generates a displacement waveform representing a change of the distance over the plurality of time phases.

Figure 7:
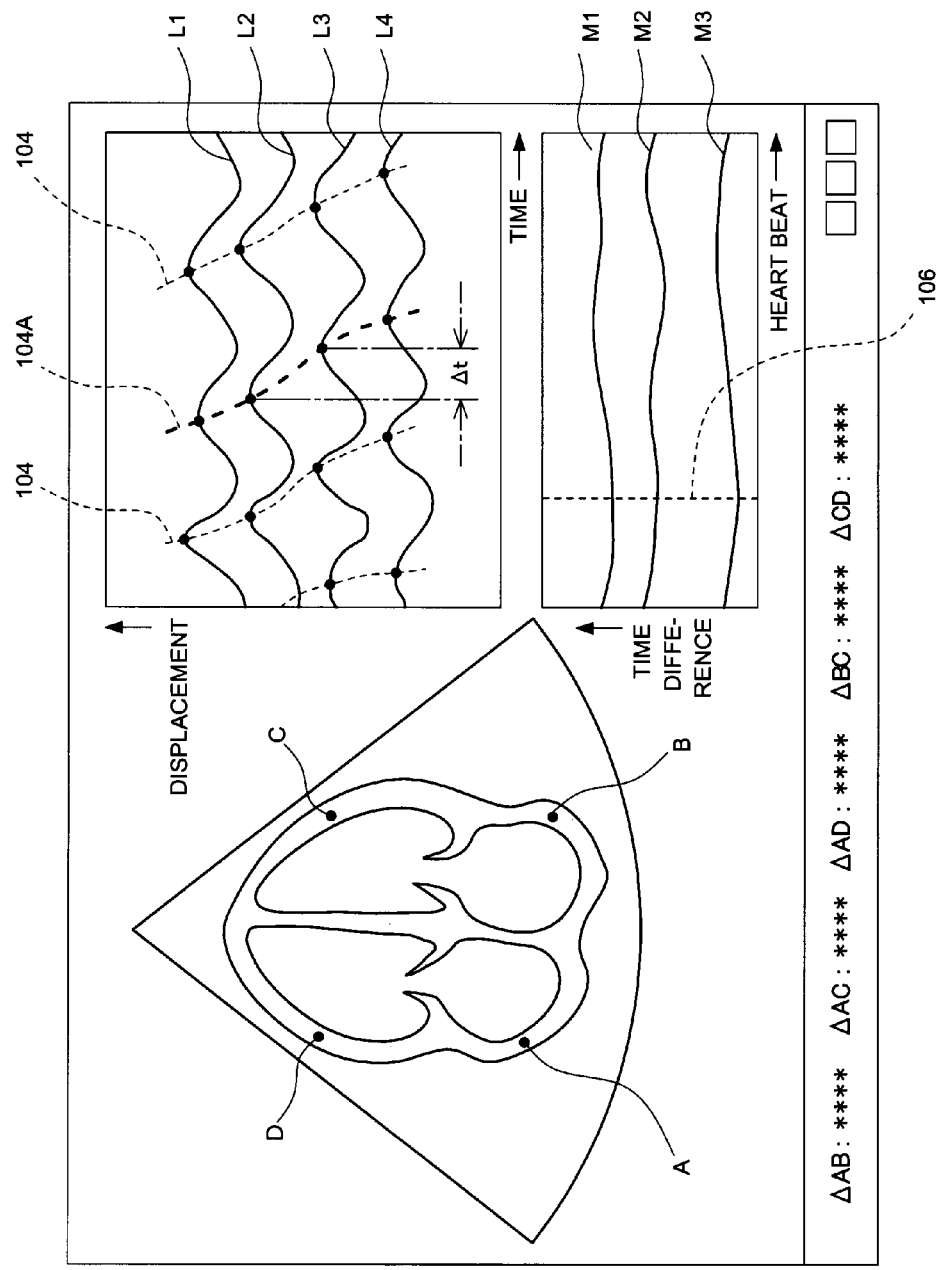
FIG. 7 is a diagram showing an example display image including a displacement waveform.

FIG. 7 is a diagram showing an example display image including the displacement waveform. FIG. 7 shows an example display image obtained when a heart is diagnosed as the target tissue. The display image of FIG. 7 includes a tomographic image related to the heart, and 4 set points A, B, C, and D which are set for the diagnosis of the heart are shown in the tomographic image.

For each set point, the movement point is searched (tracked) over a plurality of time phases, to set the fixed point F (refer to FIG. 6). In addition, for each set point, a distance from the fixed point F to each movement point P' (refer to FIG. 6) is calculated, and a displacement waveform showing a change of the distance over a plurality of time phases is generated. FIG. 7 shows an example display image including displacement waveforms L1, L2, L3, and L4 obtained from the set points A, B, C, and D, respectively.

In the present embodiment, because the fixed point F is set on the primary direction of movement over a plurality of time phases, in each displacement waveform obtained with reference to the fixed point F, an influence of movement of each set point is relatively strongly reflected and the movement of each set point is relatively sensitively represented. For the plurality of set points A, B, C, and D, the fixed point F is desirably set according to a unified reference. For example, all fixed points F for all set points are set outside of the cardiac muscle. Alternatively, all fixed points for all set points may be set inside the cardiac muscle. With this configuration, for the heart which repeats a contraction and expansion motion as a whole, a transmission status of motion can be observed based on a time difference of start of motion at set points A, B, C, and D, and the cardiac muscle can be diagnosed.

The example display image shown in FIG. 7 also includes, as an auxiliary display when the transmission status of motion is to be observed, a connection curve 104 connecting maximum value points of the displacement waveforms L1, L2, L3, and L4, graphs M1, M2 and M3 representing the time differences of motion between set points, and a cursor 106 which is used when the user designates a particular time phase.

Figure 8:
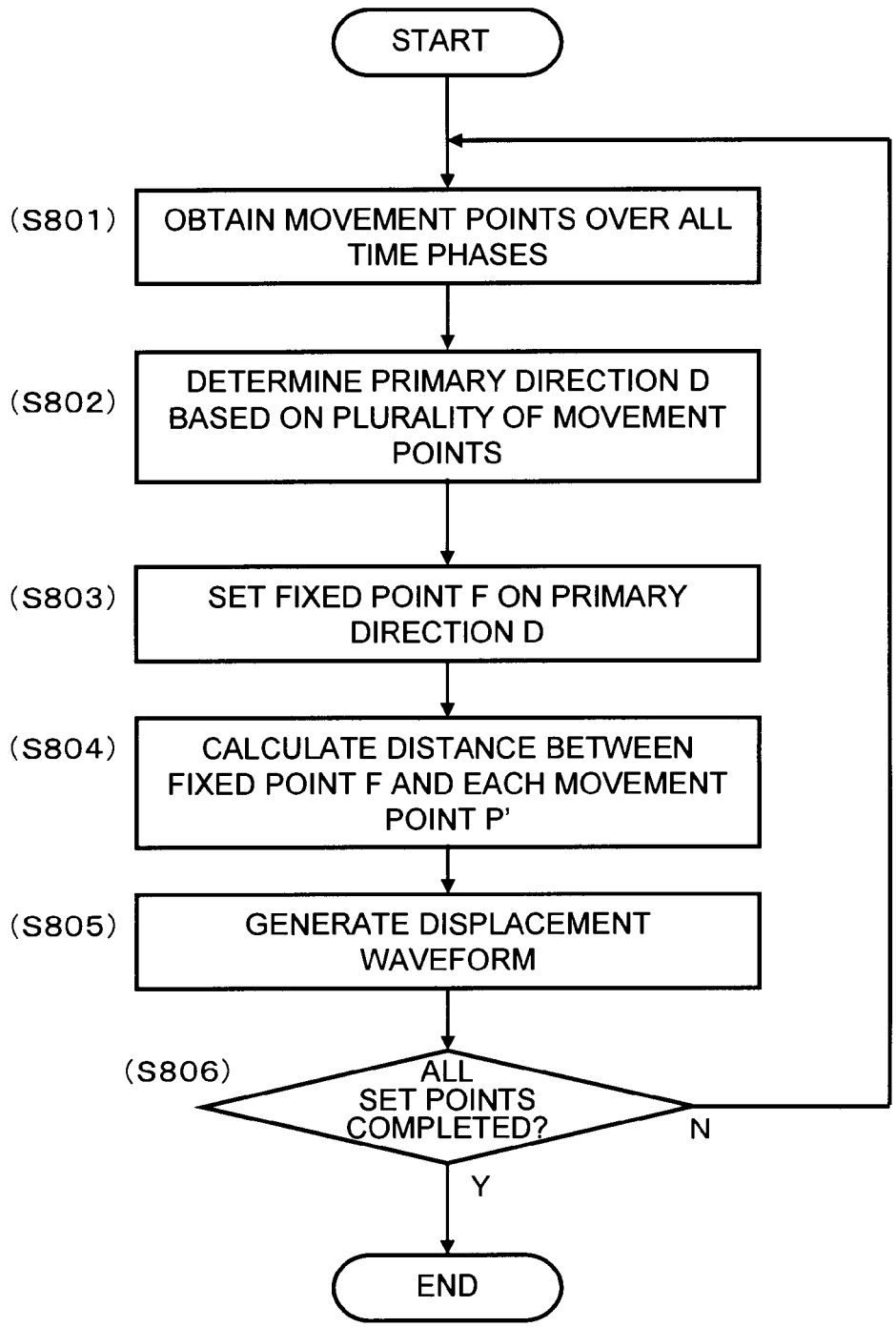
FIG. 8 is a flowchart showing a process performed in a diagnosis information generator.

FIG. 8 is a flowchart showing a process in the diagnostic information generator 40 (FIG. 1). For a certain set point, when information of movement points related to all search time phases is obtained from the pattern matching processor 30 (FIG. 1) (S801), the primary direction D of movement over the plurality of time phases for the set point is determined based on the plurality of movement points (S802; refer to FIG. 6), and the fixed point F is set on the primary direction D (S803; refer to FIG. 6). In the setting of the fixed point F, the user may designate, on the primary direction D), an outer side or an inner side of the cardiac muscle, and the fixed point F may be set according to the designation.

When the fixed point F is set, a distance between the fixed point F and each movement point P' is calculated (S804; refer to FIG. 6), and a displacement waveform representing a change of distance over a plurality of time phases is generated (S805). It is then checked whether or not processes for all set points are completed (S806), and, if the processes are not completed, the process returns to S801, and the process for the next set point is executed. When the processes from S801 to S805 are repeatedly executed and it is confirmed in S806 that processes for all set points are completed, the process at the diagnostic information generator 40 is completed, and the display image, for example, shown in FIG. 7 is displayed on the display unit 50 (FIG. 1).

An ultrasound diagnostic apparatus according to a preferred embodiment of the present invention has been described. Alternatively, for example, with programs corresponding to the processes described above and shown in FIG.

5 and in FIG. 8, the functions of the pattern matching processor 30 and the diagnostic information generator 40 shown in FIG. 1 may be realized on a computer, and the computer may be functioned as an ultrasound image processing apparatus. Moreover, the above-described preferred embodiment is merely exemplary in every aspect, and does not limit the scope of the present invention thereto. The present invention includes various modified configurations within the scope of the essentials thereof.

EXPLANATION OF REFERENCE NUMERALS

10 PROBE; 20 IMAGE PROCESSOR; 30 PATTERN MATCHING PROCESSOR; 40 DIAGNOSTIC INFORMATION GENERATOR

The invention claimed is:

1. An ultrasound image processing apparatus comprising:
    an image storage unit which stores ultrasound image data of a plurality of time phases;
    an image processor which searches image data of a search time phase for a movement point corresponding to a set point which is set in image data of a reference time phase, based on a correlation calculation between image data; and
    a diagnostic information generator which determines a primary direction of movement of the set point over a plurality of time phases based on the movement points searched over a plurality of time phases and obtains diagnostic information by evaluating the movement of the set point with the primary direction as a reference.

2. The ultrasound image processing apparatus according to claim 1, wherein
    the diagnostic information generator determines the primary direction according to a spatial variation of the movement points searched over a plurality of time phases.

3. The ultrasound image processing apparatus according to claim 1, wherein
    the diagnostic information generator sets a fixed point which becomes a reference for diagnosis on a line corresponding to the primary direction.

4. The ultrasound image processing apparatus according to claim 2, wherein
    the diagnostic information generator sets a fixed point which becomes a reference for diagnosis on a line corresponding to the primary direction.

5. The ultrasound image processing apparatus according to claim 3, wherein
    the diagnostic information generator forms a displacement waveform showing a change with respect to time of a distance from the fixed point to the movement point.

6. The ultrasound image processing apparatus according to claim 4, wherein
    the diagnostic information generator forms a displacement waveform showing a change with respect to time of a distance from the fixed point to the movement point.

7. The ultrasound image processing apparatus according to claim 1, wherein
    the image processor comprises:
    a template generation function to generate, based on a set point which is set in the image data of the reference time phase, a template corresponding to the set point;
    a search area setting function to set a search area in the image data of the search time phase;
    a correlation calculation function to execute a correlation calculation for each position in the search area while moving the template in the search area, based on image data of a template of the reference time phase and image data overlapping a template of the search time phase, and
    a movement point corresponding to the set point is searched in the search area based on a result of the correlation calculation.

8. The ultrasound image processing apparatus according to claim 7, wherein
    the diagnostic information generator determines the primary direction according to a spatial variation of the movement points searched over a plurality of time phases, sets a fixed point which becomes a reference for diagnosis on a line corresponding to the primary direction, and forms a displacement waveform showing a change with respect to time of a distance from the fixed point to the movement point.

9. The ultrasound image processing apparatus according to claim 1, wherein
    the image processor comprises:
    a template generation function to generate, based on a set point which is set in the image data of the reference time phase, a template corresponding to the set point;
    a search area setting function to set a search area in the image data of the search time phase;
    a correlation calculation function to execute a correlation calculation for each position in the search area while moving the template in the search area, based on image data of a template of the reference time phase and image data overlapping a template of the search time phase; and
    a weighting process function to apply a weighting process on a result of the correlation calculation obtained at each position in the search area based on a distance from a reference position to the each position, and
    a movement point corresponding to the set point is searched in the search area based on a result of the correlation calculation to which the weighting process is applied.

10. The ultrasound image processing apparatus according to claim 9, wherein
    the diagnostic information generator determines the primary direction according to a spatial variation of the movement points searched over a plurality of time phases.

11. The ultrasound image processing apparatus according to claim 10, wherein
    the diagnostic information generator sets a fixed point which becomes a reference for diagnosis on a line corresponding to the primary direction.

12. The ultrasound image processing apparatus according to claim 11, wherein
    the diagnostic information generator forms a displacement waveform showing a change with respect to time of a distance from the fixed point to the movement point.

13. A non-transitory computer-readable recording medium recording a program which, when executed, causes a computer which processes ultrasound image data of a plurality of time phases, to realize:
    an image processing function to search image data of a search time phase for a movement point corresponding to a set point which is set in image data of a reference time phase, based on a correlation calculation between image data; and
    a diagnostic information generation function to determine a primary direction of movement of the set point over a plurality of time phases based on the movement points searched over a plurality of time phases and to obtain diagnostic information by evaluating the movement of the set point with the primary direction as a reference.

* * * * *